United States Patent [19]

Shida et al.

[11] Patent Number: 4,919,707
[45] Date of Patent: * Apr. 24, 1990

[54] DERIVATIVE OF 1,5-DIPHENYL-1H-1,2,4-TRIAZOLE-3-CARBOXAMIDE AND HERBICIDAL COMPOSITION CONTAINING THE SAME

[75] Inventors: Takafumi Shida; Hideo Arabori; Takeo Watanabe; Yohichi Kanda; Shiro Yamazaki; Hiroyasu Shinkawa, all of Iwaki, Japan

[73] Assignee: Kureha Kagaku Kogyo Kabushiki Kaisha, Tokyo, Japan

[*] Notice: The portion of the term of this patent subsequent to Apr. 11, 2006 has been disclaimed.

[21] Appl. No.: 42,321

[22] Filed: Apr. 24, 1987

[30] Foreign Application Priority Data

Mar. 19, 1987 [JP] Japan .................................. 62-65274

[51] Int. Cl.⁵ .................. A01N 43/653; C07D 249/10
[52] U.S. Cl. ........................................ 71/92; 548/266.8
[58] Field of Search ............................ 548/262; 71/92

[56] References Cited

U.S. PATENT DOCUMENTS

| | | | |
|---|---|---|---|
| 3,681,374 | 8/1972 | Yano et al. | 548/262 |
| 4,049,812 | 9/1977 | Kuwada et al. | 514/220 |
| 4,280,831 | 7/1981 | Batel | 71/92 |
| 4,327,104 | 4/1982 | Timmler et al. | 548/262 |
| 4,492,597 | 1/1985 | Aoki et al. | 548/262 |
| 4,639,266 | 1/1987 | Heubaeh et al. | 71/92 |
| 4,820,334 | 4/1989 | Shida et al. | 71/92 |

FOREIGN PATENT DOCUMENTS

| | | | |
|---|---|---|---|
| 0128530 | 12/1984 | European Pat. Off. | |
| 0220956 | 5/1987 | European Pat. Off. | 548/262 |
| 58-185572 | 10/1983 | Japan | 548/262 |
| 61-171475 | 8/1986 | Japan | 548/262 |
| 61-210075 | 9/1986 | Japan | 548/262 |
| 2119374 | 11/1983 | United Kingdom | 548/262 |
| 2120665 | 12/1985 | United Kingdom | 548/262 |

OTHER PUBLICATIONS

Browne et al., J. of Chem. Society (London) 1962, pp. 575–583.
Sawdey, "Rearrangement of 4–Arylazo–2–etc.", Jacs, 79, p. 1955 (1957).
Okumura, "1–Phenyl–1,2,4–Triazoles", CA 86:72658U (1977).
Kadoba, "Triazolines VI: Evaluation of", J. of Pharm. Sci., 59, pp. 1190–1191 (1970).

Primary Examiner—Glennon H. Hollrah
Assistant Examiner—Patricia L. Morris
Attorney, Agent, or Firm—John P. White

[57] ABSTRACT

Disclosed herein are a derivative of 1,5-diphenyl-1H-1,2,4-triazole-3-carboxamide represented by the formula (I):

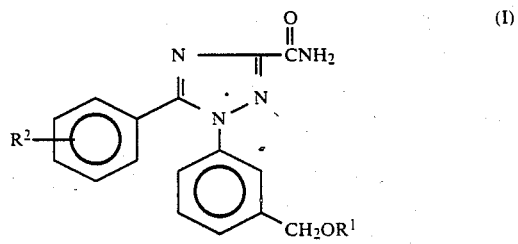

wherein $R^1$ represents a straight-chain alkyl group of 2 to 10 carbon atoms; a branched-chain alkyl group or cycloalkyl group of 3 to 10 carbon atoms; a (cycloalkyl)alkyl group of 4 to 10 carbon atoms; a non-substituted- or halogen-substituted phenyl group; an aralkyl group of 7 to 9 carbon atoms; an alkenyl group of 3 to 6 carbon atoms or an alkyl group of 2 to 10 carbon atoms, which has been substituted by 1 to 19 fluorine atoms, and $R^2$ represents a fluorine atom, a chlorine atom, a methyl group or a methoxy group and a herbicidal composition containing the derivative represented by the formula (I) as an active ingredient.

17 Claims, No Drawings

DERIVATIVE OF 1,5-DIPHENYL-1H-1,2,4-TRIAZOLE-3-CARBOXAMIDE AND HERBICIDAL COMPOSITION CONTAINING THE SAME

BACKGROUND OF THE INVENTION

The present invention relates to a derivative of 1,5-diphenyl-1H-1,2,4-triazole-3-carboxamide utilized as an active ingredient of herbicidal composition, and a herbicidal composition containing the derivative as an active ingredient.

Rice plant, wheat and corn are the important crop plants. In order to protect these crop plants from the injury of weeds and for yielding a good harvest of crops, the use of herbicide(s) is indispensable, and the development of a compound, which has an excellent selective herbicidal activity of killing only weeds without damaging the useful crop plants such as rice plant, wheat, corn etc., has been strongly demanded.

Although the derivatives of 1,5-diphenyl-1H-1,2,4-triazole-3-carboxamide and herbicidal activity thereof have been hitherto reported in Japanese Patent Applications Laying-Open (KOKAI) Nos. 57-193406 (1982), 57-193466 (1982) and 58-185572 (1983), etc., the herbicidal activity of each of the derivatives of 1,5-diphenyl-1H-1,2,4-triazole-3-carboxamide disclosed is not fully satisfiable and the selectivity thereof cannot be said to be excellent.

As a result of the present inventors' studies for developing a compound which shows an excellent herbicidal activity and at the same time, does not damage the useful crop plants such as rice plant, wheat, corn, etc., it has been found by the present inventors that a novel derivative of 1,5-diphenyl-1H-1,2,4-triazole-3-carboxamide represented by the following formula (I):

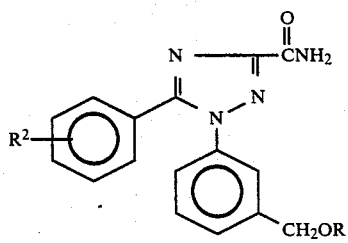

wherein $R^1$ represents a straight-chain alkyl of 2 to 10 carbon atoms, a branched-chain alkyl or cycloalkyl of 3 to 10 carbon atoms, a (cycloalkyl)alkyl group of 4 to 10 carbon atoms, a non-substituted- or halogen-substituted phenyl, an aralkyl of 7 to 9 carbon atoms, an alkenyl of 3 to 6 carbon atoms or an alkyl of 2 to 10 carbon atoms, which has been substituted by 1 to 19 fluorine atoms and $R^2$ represents a fluorine atom, a chlorine atom, a methyl or a methoxy, has an excellent selective herbicidal activity, and on the basis of this finding, the present inventors have achieved the present invention.

Namely, the object of the present invention lies in providing a novel derivative of 1,5-diphenyl-1H-1,2,4-triazole-3-carboxamide, which shows an excellent herbicidal activity to the graminous weeds and broad-leaved weeds, particularly to broad-leaved weeds and on the other hand, shows practically no phytotoxicity to the crop plants such as rice plant, wheat, corn, etc., and a herbicidal composition containing the derivative as an active ingredient.

SUMMARY OF THE INVENTION

In a first aspect of the invention, there is provided a derivative of 1,5-diphenyl-1H-1,2,4-triazole-3-carboxamide represented by the formula (I):

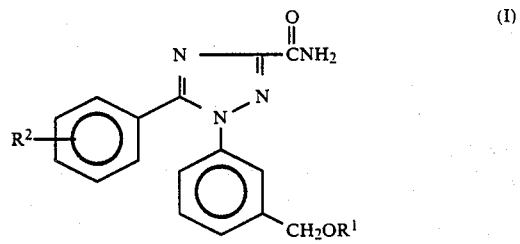

wherein $R^1$ represents a straight-chain alkyl group of 2 to 10 carbon atoms; a branched-chain alkyl group or cycloalkyl group of 3 to 10 carbon atoms; a (cycloalkyl)alkyl group of 4 to 10 carbon atoms; a non-substituted- or halogen-substituted phenyl group; an aralkyl group of 7 to 9 carbon atoms; an alkenyl group of 3 to 6 carbon atoms or an alkyl group of 2 to 10 carbon atoms, which has been substituted by 1 to 19 fluorine atoms, and $R^2$ represents a fluorine atom, a chlorine atom, a methyl group or a methoxy group.

In a second aspect of the invention, there is provided a herbicidal composition comprising a herbicidally effective amount of a derivative of 1,5-diphenyl-1H-1,2,4-triazole-3-carboxamide represented by the formula (I) as an active ingredient:

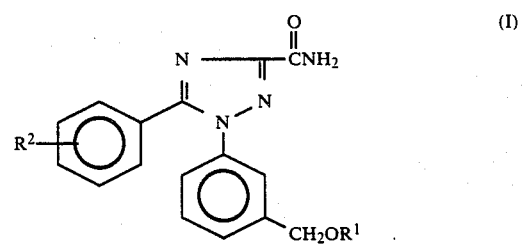

wherein $R^1$ represents a straight-chain alkyl group of 2 to 10 carbon atoms; a branched-chain alkyl group or cycloalkyl group of 3 to 10 carbon atoms; a (cycloalkyl)alkyl group of 4 to 10 carbon atoms; a non-substituted- or halogen-substituted phenyl group; an aralkyl group of 7 to 9 carbon atoms; an alkenyl group of 3 to 6 carbon atoms or an alkyl group of 2 to 10 carbon atoms, which has been substituted by 1 to 19 fluorine atoms, and $R^2$ represents a fluorine atom, a chlorine atom, a methyl group or a methoxy group, and a herbicidally acceptable carrier or adjuvant.

In a third aspect of the invention, there is provided a process for producing a derivative of 1,5-diphenyl-1-H-1,2,4-triazole-3-carboxamide represented by the formula (I):

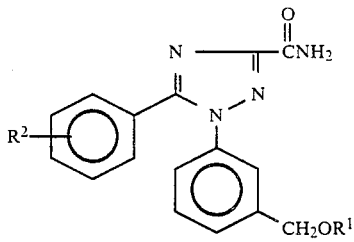

wherein R¹ represents a straight-chain alkyl group of 2 to 10 carbon atoms; a branched-chain alkyl group or cycloalkyl group of 3 to 10 carbon atoms; a (cycloalkyl)alkyl group of 4 to 10 carbon atoms; a non-substituted- or halogen-substituted phenyl group; an aralkyl group of 7 to 9 carbon atoms; an alkenyl group of 3 to 6 carbon atoms or an alkyl group of 2 to 10 carbon atoms, which has been substituted by 1 to 19 fluorine atoms, and R² represents a fluorine atom, a chlorine atom, a methyl group or a methoxy group, which process comprises:

(1) reacting 3-chloromethyl-1-nitrobenzene represented by the formula (III):

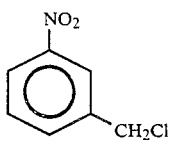

with a compound represented by the formula:

wherein R¹ represents the same meaning as above, at a temperature of −10° to 150° C. in the presence of an acceptor for hydrogen chloride formed;

(2) reducing the thus obtained nitrobenzyl ether represented by the formula (IV):

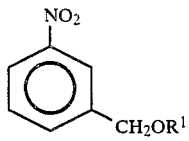

wherein R¹ represents the same meaning as above, (3) diazotizing the thus obtained aniline compound represented by the formula (V):

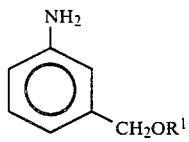

wherein R¹ represents the same meaning as above; and (4) diazocoupling the thus obtained diazonium salt represented by the formula:

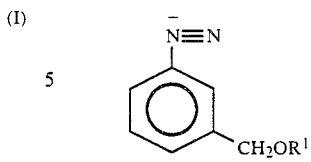

wherein R¹ represents the same meaning as above, with a derivative of 2-phenyl-2-oxazolin-5-one represented by the formula (VI):

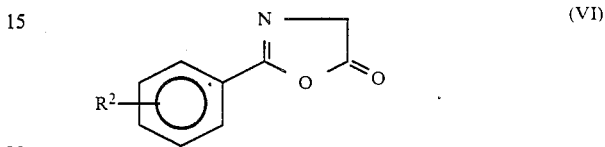

wherein R² represents the same meaning as above, at a temperature of −50° to 100° C. for 0.1 to 20 hours.

DETAILED DESCRIPTION OF THE INVENTION

The present invention relates to a derivative of 1,5-diphenyl-1H-1,2,4-triazole-3-carboxamide represented by the following formula (I):

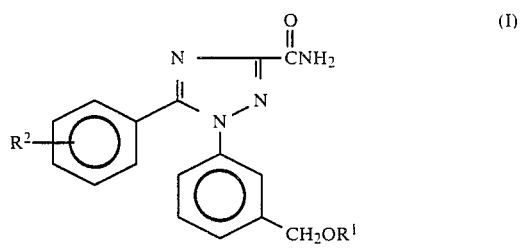

and a herbicidal composition containing the derivative as an active ingredient.

In the above-mentioned formula (I), R¹ represents a straight-chain alkyl group of 2 to 10, preferably 3 to 6 carbon atoms, a branched-chain alkyl group or cycloalkyl group of 3 to 10, preferably 3 to 7 carbon atoms, a (cycloalkyl)alkyl group of from 4 to 10 carbon atoms, preferably an alkyl group of 1 to 3 carbon atoms having a cycloaliphatic structure of 3 to 7 carbon atoms, a phenyl group which has not been substituted or substituted by halogen atom(s), preferably 1 to 3 chlorine and/or fluorine atoms, an aralkyl group of 7 to 9 carbon atoms, an alkenyl group of 3 to 6 carbon atoms or an alkyl group of 2 to 10, preferably from 2 to 6 carbon atoms, which has been substituted by 1 to 19, preferably from 3 to 12 fluorine atoms and R² represents a fluorine atom, a chlorine atom, a methyl group or a methoxy group.

The compounds represented by the formula (I) according to the present invention are exemplified in the following Table 1. Table 2 shows the melting points, the results of spectroscopic analysis and elementary analysis of the thus exemplified compounds.

TABLE 1

$$\text{Structure (I): } R^2\text{-phenyl-C(=N-N(-phenyl-CH}_2\text{OR}^1\text{)-)=CH-CONH}_2$$

| Compound No. | R¹ | R² |
|---|---|---|
| 1 | —CH₂(CH₂)₂CH₃ | 2-F |
| 2 | —CH₂(CH₂)₃CH₃ | 2-F |
| 3 | —CH₂CH₂CH(CH₃)₂ | 2-F |
| 4 | —CH₂CH₂CH(CH₃)₂ | 3-F |
| 5 | —CH₂CH₂CH(CH₃)₂ | 4-F |
| 6 | —CH₂CH(CH₃)CH₂CH₃ | 2-F |
| 7 | —CH₂C(CH₃)₃ | 2-F |
| 8 | —CH₂(CH₂)₄CH₃ | 2-F |
| 9 | —CH₂-cyclohexyl | 2-F |
| 10 | —CH₂-(methylphenyl) | 2-F |
| 11 | —CH₂-(fluorophenyl) | 2-F |
| 12 | —(4-chlorophenyl) | 2-F |
| 13 | —CH₂-phenyl | 2-F |
| 14 | —CH₂CH=CH₂ | 2-F |
| 15 | —CH₂CF₃ | 2-F |
| 16 | —CH₂CF₂CHF₂ | 2-F |
| 17 | —CH₂CF₂CF₃ | 2-F |
| 18 | —CH₂CF₂CF₃ | 3-F |
| 19 | —CH₂CF₂CF₃ | 4-F |
| 20 | —CH₂CF₂CHFCF₃ | 2-F |
| 21 | —CH₂(CF₂)₂CF₃ | 2-F |
| 22 | —CH₂(CF₂)₂CF₃ | 3-F |
| 23 | —CH₂(CF₂)₂CF₃ | 4-F |
| 24 | —CH₂(CF₂)₃CHF₂ | 2-F |
| 25 | —CH₂(CF₂)₅CHF₂ | 2-F |
| 26 | —CH₂CH₂CH(CH₃)₂ | 4-Cl |
| 27 | —CH₂CF₂CF₃ | 4-Cl |
| 28 | —CH₂(CF₂)₂CF₃ | 4-Cl |
| 29 | —CH₂CH₂CH(CH₃)₂ | 4-CH₃ |
| 30 | —CH₂CF₂CF₃ | 4-CH₃ |
| 31 | —CH₂(CF₂)₂CF₃ | 4-CH₃ |
| 32 | —CH₂CH₂CH(CH₃)₂ | 4-OCH₃ |
| 33 | —CH₂(CF₂)₂CF₃ | 4-OCH₃ |
| 34 | —CH₂CH₃ | 2-F |

TABLE 2

| Compound No. | Melting Point (°C.) | IR (KBr, cm⁻¹) and NMR (d₆-DMSO, δ, ppm, 60 MHz) | C (%) Found/Calc | H (%) Found/Calc | N (%) Found/Calc |
|---|---|---|---|---|---|
| 1 | 133–134 | IR: 3470 3300 1675<br>NMR*: 0.88 (3H, t, 6Hz) 1.1–1.76 (4H, m)<br>3.3 (2H, t, 6Hz) 4.36 (2H, s)<br>6.36 (1H, bs) 6.73–7.73 (9H, m) | 65.01 / 65.21 | 5.90 / 5.75 | 15.40 / 15.21 |
| 2 | 69–70 | IR: 3400 3300 1680 1580<br>NMR: 0.85 (3H, t, 6Hz) 1.06–1.63 (6H, m)<br>3.2–3.38 (2H, m) 4.36 (2H, s)<br>6.96–7.76 (9H, m) 7.76–8 (1H, bs) | 65.92 / 65.95 | 5.90 / 6.06 | 14.83 / 14.65 |
| 3 | 51–53 | IR: 3450 3350 1670<br>NMR*: 0.86 (6H, d, 7Hz) 1.06–1.7 (3H, m)<br>3.36 (2H, t, 7Hz) 4.4 (2H, s)<br>6.23 (1H, bs) 6.9–7.8 (9H, m) | 65.96 / 65.95 | 5.86 / 6.06 | 14.62 / 14.65 |
| 4 | 122–123 | IR: 3450 3140 1690 1480<br>NMR: 0.83 (6H, d, 6Hz) 1.15–1.76 (3H, m)<br>3.36 (2H, t, 6Hz) 4.43 (2H, s)<br>7.1–7.96 (10H, m) | 65.90 / 65.95 | 5.88 / 6.06 | 14.66 / 14.65 |
| 5 | 105–106 | IR: 3440 1700 1470<br>NMR: 0.83 (6H, d, 6Hz) 1.13–1.67 (3H, m)<br>3.36 (2H, t, 6Hz) 4.43 (2H, s)<br>6.93–7.93 (10H, m) | 65.93 / 65.95 | 5.87 / 6.06 | 16.64 / 14.65 |
| 6 | 65–67 | IR: 3460 3325 1680<br>NMR: 0.80 (3H, t, 6Hz) 0.85 (3H, d, 6Hz)<br>1–1.9 (3H, m) 3.15 (2H, d, 5Hz)<br>4.40 (2H, s) 6.95–8.11 (10H, m) | 65.92 / 65.95 | 5.87 / 6.06 | 14.49 / 14.65 |
| 7 | 143–144 | IR: 3460 1670 1580<br>NMR: 0.81 (9H, s) 2.98 (2H, s)<br>4.41 (2H, s) 6.96–7.75 (9H, m) | 65.94 / 65.95 | 5.91 / 6.06 | 14.83 / 14.65 |

TABLE 2-continued

| Compound No. | Melting Point (°C.) | IR (KBr, cm$^{-1}$) and NMR (d$_6$-DMSO, δ, ppm, 60 MHz) | Elementary Analysis Found Calculated | | |
|---|---|---|---|---|---|
| | | | C (%) | H (%) | N (%) |
| 8 | 88–90 | 7.75–7.98 (1H, bs)<br>IR: 3400 2920 2850 1690 1670<br>NMR: 0.85 (3H, t, 6Hz) 1.03–1.87 (8H, m)<br>3.33 (2H, t, 6Hz) 4.43 (2H, s)<br>6.87–8.1 (10H, m) | 66.74<br>66.65 | 6.49<br>6.36 | 14.14<br>14.13 |
| 9 | 99–100 | IR: 3460 3320 1675<br>NMR: 0.52–2.15 (11H, m) 3.13 (2H, d, 5Hz)<br>4.40 (2H, s) 6.97–8.27 (10H, m) | 67.48<br>67.63 | 5.99<br>6.17 | 13.54<br>13.72 |
| 10 | 103–105 | IR: 3440–3350 (br) 1680 1590<br>NMR*: 5.02 (2H, s) 6.72–7.9 (15H, m) | 68.23<br>68.03 | 4.44<br>4.41 | 14.37<br>14.42 |
| 11 | 121–123 | IR: 3350–3220 (br) 1680 1660 1210<br>1030 NMR*: 4.9 (2H, s) 5.97 (1H, bs)<br>6.7–7.53 (13H, m) | 65.04<br>65.02 | 4.15<br>3.97 | 13.71<br>13.79 |
| 12 | 173–174 | IR: 3350 3220 1680 1660<br>NMR: 5.13 (2H, s) 6.88–8.13 (14H, m) | 62.54<br>62.49 | 3.90<br>3.81 | 13.35<br>13.25 |
| 13 | 125–126 | IR: 3470 3300 1700 1660<br>NMR: 4.41 (2H, s) 4.48 (2H, s)<br>6.93–7.78 (14H, m) 7.78–8 (1H, bs) | 68.85<br>68.65 | 4.67<br>4.76 | 14.09<br>13.92 |
| 14 | 165–167 | IR: 3440 3280 1685<br>NMR: 3.8–4.1 (2H, m) 4.33 (2H, s)<br>4.87–5.33 (2H, m) 5.47–6.23 (1H, m)<br>6.93–8.00 (10H, m) | 64.86<br>64.77 | 4.66<br>4.86 | 16.09<br>15.90 |
| 15 | 123–124 | IR: 3450 3350 1660 1275<br>NMR*: 3.93 (2H, q, 9Hz) 4.6 (2H, s)<br>7–7.9 (10H, m) | 55.03<br>54.83 | 3.39<br>3.58 | 14.08<br>14.21 |
| 16 | 116–117 | IR: 3460 1705 1675<br>NMR*: 3.7 (2H, tt, 14Hz, 2Hz) 4.53 (2H, s)<br>5.76 (1H, tt, 53Hz, 6Hz) 6.6–7.93 (10H, m) | 53.71<br>53.53 | 3.39<br>3.55 | 13.04<br>13.14 |
| 17 | 82–84 | IR: 3360 1670 1200<br>NMR*: 3.78 (2H, tq, 13Hz, 2Hz)<br>4.55 (2H, s) 6.26 (1H, bs)<br>6.73–7.9 (9H, m) | 51.16<br>51.36 | 3.24<br>3.18 | 12.69<br>12.61 |
| 18 | 156–157 | IR: 3450 3140 1690<br>NMR: 4.17 (2H, tq, 14Hz, 2Hz)<br>4.75 (2H, s) 7.1–8.1 (10H, m) | 51.13<br>51.36 | 3.25<br>3.18 | 12.71<br>12.61 |
| 19 | 108–110 | IR: 3480 3190 1690<br>NMR: 4.07 (2H, tq, 14Hz, 2Hz)<br>4.69 (2H, s) 7–8 (10H, m) | 51.19<br>51.36 | 3.23<br>3.18 | 12.67<br>12.61 |
| 20 | 70–72 | IR: 3450 3360 1680<br>NMR*: 3.2–4 (2H, m) 4.55 (2H, s)<br>4.95 (1H, d 6-plet, 50Hz, 6Hz)<br>6.45–7.78 (10H, m) | 50.63<br>50.43 | 3.24<br>3.17 | 11.57<br>11.76 |
| 21 | 90–91 | IR: 3450 3350 1660 1220<br>NMR: 4.06 (2H, tt, 13Hz, 2Hz)<br>4.66 (2H, s) 6.95–8.03 (10H, m) | 48.76<br>48.59 | 2.80<br>2.85 | 11.38<br>11.33 |
| 22 | 130–131 | IR: 3450 3280 3150 1690 1600<br>NMR: 4.11 (2H, tt, 14Hz, 2Hz)<br>4.7 (2H, s) 7–8 (10H, m) | 48.79<br>48.59 | 2.79<br>2.85 | 11.36<br>11.33 |
| 23 | 86–88 | IR: 3380 1680 1600<br>NMR: 4.13 (2H, tt, 14Hz, 2Hz)<br>4.69 (2H, s) 7–8 (10H, m) | 48.73<br>48.59 | 2.81<br>2.85 | 11.41<br>11.33 |
| 24 | 99–101 | IR: 3400 3280 3200 1685 1170<br>NMR: 4.03 (2H, tt, 15Hz, 2Hz)<br>4.8 (2H, s) 6.03 (1H, tt, 52Hz, 6Hz)<br>6.86–7.9 (10H, m) | 48.12<br>47.92 | 2.79<br>2.87 | 10.57<br>10.64 |
| 25 | Paste | IR: 3460 3245 1685<br>NMR: 4.10 (2H, tt, 14Hz, 2Hz)<br>4.67 (2H, s) 6.27 (1H, tt, 55Hz, 5Hz)<br>6.65–8.25 (10H, m) | 44.29<br>44.10 | 2.25<br>2.41 | 9.14<br>8.94 |
| 26 | 110–111 | IR: 3430 1690 1450<br>NMR: 0.83 (6H, d, 6Hz) 1.06–1.6 (3H, m)<br>3.36 (2H, t, 6Hz) 4.43 (2H, s)<br>7.16–7.7 (9H, m) 7.7–8 (1H, bs) | 63.37<br>63.23 | 5.75<br>5.81 | 14.15<br>14.05 |
| 27 | 119–121 | IR: 3460 3170 3100 1680 1590<br>NMR: 4.1 (2H, tq, 14Hz, 2Hz)<br>4.69 (2H, s) 7.2–8.1 (10H, m) | 49.35<br>49.53 | 2.92<br>3.06 | 12.32<br>12.16 |
| 28 | 168–169 | IR: 3460 3270 3190 1690<br>NMR: 4.11 (2H, tt, 15Hz, 2Hz) 4.7 (2H, s)<br>7.13–8 (10H, m) | 46.87<br>47.03 | 2.88<br>2.76 | 11.02<br>10.97 |
| 29 | 94–97 | IR: 3390 3160 1695 1470<br>NMR: 0.81 (6H, d, 6Hz) 1.08–1.7 (3H, m)<br>2.28 (3H, s) 3.35 (2H, t, 6Hz)<br>4.41 (2H, s) 6.93–7.9 (10H, m) | 69.64<br>69.82 | 6.79<br>6.92 | 14.95<br>14.80 |
| 30 | 140–142 | IR: 3460 3150 1690 1600<br>NMR: 2.31 (3H, s) 4.1 (2H, tq, 14Hz, 2Hz)<br>4.7 (2H, s) 6.9–8 (10H, m) | 54.37<br>54.55 | 4.08<br>3.89 | 12.92<br>12.72 |
| 31 | 144–145 | IR: 3440 3150 1700 1610<br>NMR: 2.28 (3H, s) 4.11 (2H, tt, 14Hz, 2Hz) | 51.29<br>51.44 | 3.42<br>3.49 | 11.61<br>11.42 |

TABLE 2-continued

| Compound No. | Melting Point (°C.) | IR (KBr, cm$^{-1}$) and NMR (d$_6$-DMSO, δ, ppm, 60 MHz) | Elementary Analysis Found Calculated | | |
|---|---|---|---|---|---|
| | | | C (%) | H (%) | N (%) |
| 32 | 98–101 | 4.69 (2H, s) 7–8 (10H, m) IR: 3440 1680 1600 NMR: 0.83(6H,d,6Hz) 1.1–1.66(3H,m) 3.38(2H,t,6Hz) 3.73(3H,s) 4.45(2H,s) 6.9(2H,d,9Hz) 7.1–7.66(5H,m) 7.38 (2H,d,9Hz) 7.66–7.93 (1H,bs) | 66.95 66.99 | 6.81 6.64 | 14.13 14.20 |
| 33 | 147–148 | IR: 3440 3370 3150 1690 1610 NMR: 3.75 (3H, s) 4.14 (2H, tt, 14Hz, 2Hz) 4.71 (2H, s) 6.9 (2H, d, 9Hz) 7.2–7.93 (8H, m) | 50.01 49.81 | 3.52 3.38 | 10.94 11.06 |
| 34 | 120–122 | IR: 3350 3270 1695 1665 NMR: 1.13 (3H, t, 7Hz) 3.44 (2H, q, 7Hz) 4.53 (2H, s) 7.17–7.90 (8H, m) 7.90 (1H, s) 8.18 (1H, s) | 63.64 63.52 | 5.05 5.03 | 16.65 16.46 |

Note:
*means CDCl$_3$ was used as a solvent.

Since each of the compounds represented by the formula (I), preferably compound Nos. 1–3, 6–9, 15–17, 20, 21, 24 and 25, has an excellent selective herbicidal activity, it can be utilized in crop fields and paddy fields as an active ingredient of a herbicidal composition.

The compound represented by the formula (I) according to the present invention can be manufactured by the process shown in the following reaction scheme 1.

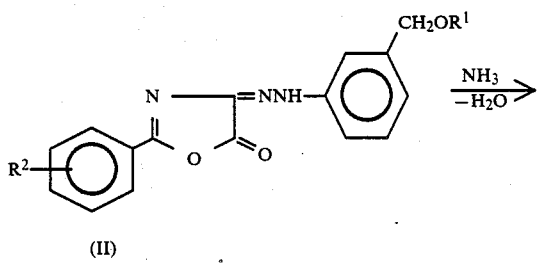

(II)

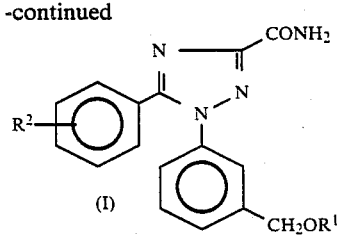

(I)

Reaction scheme 1, wherein R$^1$ and R$^2$ respectively represent the same meaning as that described before.

Namely, a derivative of 2-phenyl-4-phenylhydrazono-2-oxazolin-5-one represented by the formula (II) is reacted with ammonia in organic solvent such as toluene and acetone at a temperature of −10° to 50° C., preferably 0° to 30° C., for 0.1 to 10 hours. Then, after the reaction mixture is acidified with acid such as hydrochloric acid and acetic acid, dehydrating ring closure is carried out with stirring at a temperature of 0° to 150° C., preferably 20° to 80° C., for 0.1 to 10 hours, thereby manufacturing the compound represented by the formula (I) in a high yield.

The compound represented by the formula (II) can be synthesized according to the process shown in the following reaction scheme 2.

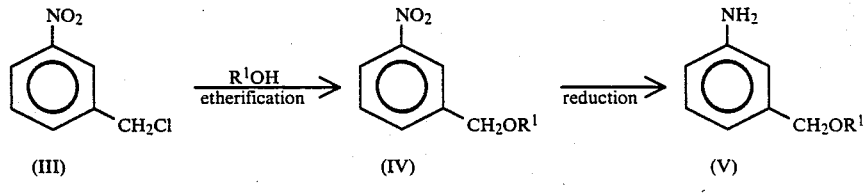

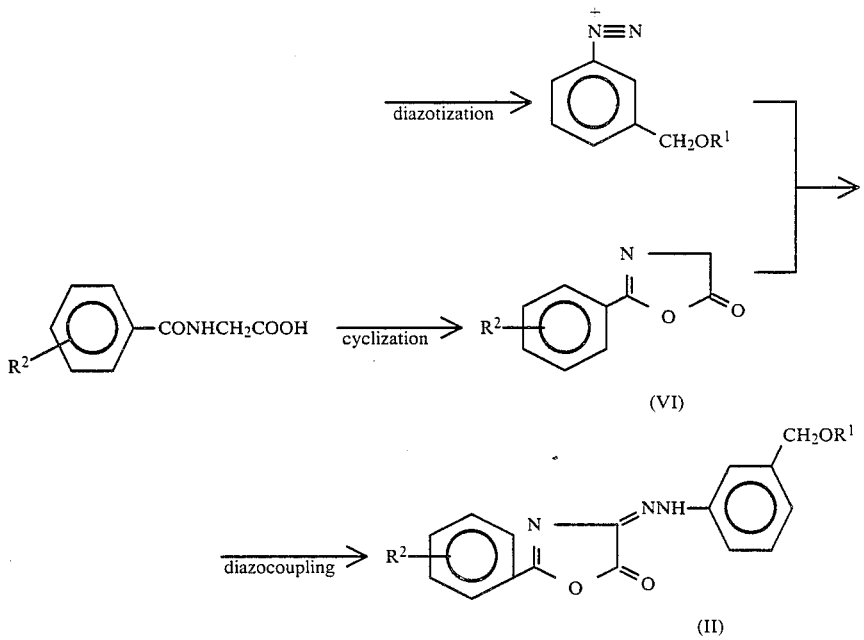

Reaction scheme 2, wherein $R^1$ and $R^2$ respectively represent the same meaning as that described before.

Namely, 3-chloromethyl-1-nitrobenzene (III) is reacted with a compound represented by the formula:

$R^1OH$ wherein $R^1$ has the same meaning as above, in a solvent such as dimethylformamide, hexamethylphosphoramide, etc. for 0.1 to 20 hour, preferably 0.5 to 10 hours, at a temperature of −10° to 150° C., preferably 0° to 80° C., in the presence of an acceptor for hydrogen chloride formed such as KOH, NaH, etc. to obtain a nitrobenzyl ether (IV). The thus obtained nitrobenzyl ether (IV) is reduced by various well known methods. For instance, the nitrobenzyl ether (IV) is heated under reflux after adding hydrazine hydrate in alcohol for 1 to 10 hours in the presence of palladium-charcoal, to convert the compound to an aniline compound (V). Then the aniline compound is diazotized by, for example, sodium nitrite in hydrochloric acid at a temperature of −10° to 15° C. to obtain diazonium salt.

Separately, a derivative of 2-phenyl-2-oxazolin-5-one (VI) is synthesized by subjecting a derivative of hippuric acid to dehydrating-cyclization in acetic anhydride at a temperature of 20° to 100° C., preferably 50° to 90° C., for 0.1 to 30 hours, preferably 0.1 to 3 hours. Then the diazonium salt is reacted with the derivative of 2-phenyl-2-oxazolin-5-one at a temperature of −50° to 100° C., preferably −30° to 40° C., for 0.01 to 20 hours, preferably 0.1 to 10 hours to obtain the compound represented by the formula (II).

The derivative of 1,5-diphenyl-1H-1,2,4-triazole-3-carboxamide according to the present invention is used singly as a herbicide, or used as a herbicidal composition such as wettable powders, emulsions, granules and powders while using a carrier (diluent) and/or an adjuvant, which have (has) been hitherto used for the preparation of agricultural chemicals.

The content of the derivative of 1,5-diphenyl-1H-1,2,4-triazole-3-carboxamide according to the present invention in a herbicidal composition is 0.1 to 50% by weight.

The derivative of 1,5-diphenyl-1H-1,2,4-triazole-3-carboxamide according to the present invention or a herbicidal composition containing the derivative as an active ingredient is applied onto the soil of a paddy field and a crop field and/or weeds so that 0.1 to 500 g of the derivative is applied per 10 acres.

The present invention will be explained more precisely while referring to the following non-limitative examples.

SYNTHETIC EXAMPLE 1

Synthesis of 1-(3-methylbutoxy)methyl-3-nitrobenzene

Into a mixture of 500 ml (4.59 mol) of 3-methyl-1-butanol and 140 ml of dimethylformamide, 158.1 g (0.92 mol) of 3-chloromethylnitrobenzene was dissolved, and 78 g (1.39 mol) of potassium hydroxide pellets was added to the thus formed solution while cooling with water under a vigorous stirring. The temperature of the reaction mixture rised to 43° C. and then dropped slowly to room temperature. Thereafter, the reaction mixture was stirred for 7 hours at room temperature to complete the reaction.

After removing the solid matters in the liquid reaction mixture by filtration and adjusting the filtrate to pH 2 by hydrochloric acid, the excess alcohol and dimethylformamide were distilled off from the thus adjusted filtrate. After dissolving the residue into a mixture of 450 ml of n-hexane and 50 ml of ethyl acetate, and washing the solution with 1N HCl and an aqueous saturated solution of sodium chloride successively, the thus washed solution was dried over anhydrous magnesium sulfate.

After distilling the solvent off from the thus dried solution, the residual liquid was subjected to fractional distillation to collect 182.2 g of a fraction at 116°-117° C. (0.08 mmHg) to obtain 1-(3-methylbutoxy)-methyl-3-nitrobenzene in a yield of 90.1%.

SYNTHETIC EXAMPLE 2

Synthesis of 3-[(3-methylbutoxy)methyl]aniline

Into 150 ml of ethanol, 130 g (0.58 mol) of 1-(3-methylbutoxy)methyl-3-nitrobenzene obtained in Synthetic Example 1 was dissolved, and 0.6 g of 10% palladiumcharcoal was added to the thus formed solution. Into the thus treated solution, 89 ml (1.84 mol) of hydrazine hydrate was dropped such a speed that violent foaming is not caused. After ending the dropping, the reaction mixture was refluxed for 3 hours on a hot water bath to complete the reaction. After cooling the liquid reaction product by allowing to stand, the catalyst was removed from the reaction mixture by filtration, and the thus removed catalyst was washed with ethanol.

After condensing the filtrate together with the ethanol washings, the condensate was dissolved into 300 ml of dichloromethane and after washing the thus formed solution with an aqueous 10% sodium carbonate solution, then with an aqueous saturated sodium chloride solution, the thus washed solution was dried over anhydrous potassium carbonate. By distilling the solvent off from the thus dried solution and fractionally distilling the residue, 109.2 g of a fraction boiling at 105° to 106° C. (0.19 mmHg) were collected to obtain 3-[(3-methylbutoxy)methyl]aniline in a yield of 97.1%.

SYNTHETIC EXAMPLE 3

Synthesis of 2-(2-fluorophenyl)-4-[3-[(3-methylbutoxy)-methyl]-phenyl]hydrazono-2-oxazolin-5-one After preparing 2-(2-fluorophenyl)-2-oxazolin-5-one by stirring the mixture of 3.94 g of 2-fluorohippuric acid, 3.28 g of sodium acetate and 17.4 ml of acetic anhydride for 20 min at 60° C., the mixture was rapidly cooled in iced water.

Separately, a solution of a diazonium salt was prepared by adding 2.8 ml of isopentyl nitrite to a mixture of 3.48 g (18 mmol) of 3-[(3-methylbutoxy)methyl]aniline, 3.4 ml of 35% hydrochloric acid and 12 ml of acetic acid under cooling with iced water and under agitation for 10 min.

Into the mixture of 2-(2-fluorophenyl)-2-oxazolin-5-one, the thus prepared solution of the diazonium salt was added within 2 min while stirring the mixture under cooling with iced water, and the thus formed mixture was stirred for 2 hours. Thereafter, 40 ml of iced water and 20 ml of petroleum ether were added to the reaction mixture and the mixture was stirred for 2 hours. The precipitated orange-coloured substance was collected by filtration of the reaction mixture to obtain 2.45 g of 2-(2-fluorophenyl)-4-[3-[(3-methylbutoxy)methyl]-phenyl]hydrazono-2-oxazolin-5-one in a yield of 35.5%.

EXAMPLE 1

Synthesis of 5-(2-fluorophenyl)-1-[3-(3-methylbutoxy)methyl]phenyl-1H-1,2,4-triazole-3-carboxamide (Compound No. 3)

Into 25 ml of acetone, 1.5 g of 4-[3[(3-methylbutoxy)-methyl]phenyl]hydrazono-2-(2-fluorophenyl)-2-oxazolin-5-one obtained in Synthetic Example 3 was dissolved, and while stirring the thus formed solution at room temperature, 0.5 ml of aqueous 28% solution of ammonia was added thereto, and the mixture was stirred for 10 min to obtain a slurry-like mixture. To the thus obtained slurry-like mixture, 0.5 ml of 35% hydrochloric acid was added and the mixture was heated for 10 min under reflux. The reaction mixture was added to 200 ml of water, and the precipitated pale brown substances were collected by filtration. On adding the thus collected pale brown material to 20 ml of a 1:5 solvent mixture of ethyl acetate and n-hexane, the colour of the substances transferred to the liquid phase and a colourless solid was obtained. By collecting the solid by filtration and air-drying the thus collected solid, 1.08 g of 5-(2-fluorophenyl)-1-[3-(3-methylbutoxy)methyl]phenyl-1H-1,2,4-triazole-3-carboxamide were obtained in a yield of 72%.

EXAMPLE 2

Preparation of a herbicidal composition of wettable powder:

50 parts of Compound No. 3,
5 parts of a salt of ligninsulfonic acid,
3 parts of a salt of alkylsulfonic acid and
42 parts of diatomaceous earth.

The above substances was pulverized to obtain a herbicidal composition of a wettable powder form.

The herbicidal composition is applied after diluting with water.

EXAMPLE 3

Preparation of a herbicidal composition of emulsion:

25 parts of Compound No. 3,
65 parts of xylene and
10 parts of polyoxyethylene alkyl allyl ether.

The above substances were uniformly blended to obtain a herbicidal composition of an emulsion.

The herbicidal composition is applied after diluting with water.

EXAMPLE 4

Preparation of a herbicidal composition of granule:

8 parts of Compound No. 17,
40 parts of bentonite,
45 parts of clay and
7 parts of ligninsulfonic acid.

The above substances were uniformly blended and after adding water to the thus formed blend, the mixture was kneaded and extruded into granules by using an extruding pelletizer.

The thus extruded granules were dried to be the herbicidal composition of granule form.

TEST EXAMPLE 1

Effect on the weeds in the crop field (pre-emergence treatment)

A planter of the dimensions of 650×210×220 mm was filled with soil in a state of a crop field, and after sowing a predetermined amount of the seeds of *Amaranthus retroflexus, Bidens pilosa* var. *pilosa, Brassica arvensis, Stellaria media, Solanum nigrum, Abutilon theophrasti, Echinochloa Crus-galli* var. *frumentacea, Digitaria sanguinalis*, wheat and corn on the thus filled soil and covering the thus sown seeds with hte soil, a dilution (prepared by diluting a wettable powder prepared in the same manner as in Example 2 to a predetermined concentration with water) was uniformly applied onto the soil of the planter in an amount corresponding to 200 g of the active ingredient (the present compound) of the wettable powder per 10 are of the surface of the soil in the planter, and thereafter, the thus treated planter was kept in a glass house at ordinary temperature to observe the growth state of the thus sown seeds.

On the 21st day of the treatment, the herbicidal effect of the wettable powder to each of the weeds and the phytotoxicity of the wettable powder to each of the crop plants were observed, and after evaluating the herbicidal effect and the phytotoxicity according to the following ratings, the results shown in Table 3 was obtained.

Ratings of evaluation:
(1) Herbicidal effect:
0 ... no herbicidal effect
1 ... not more than 30% of herbicidal effect
2 ... from 31 to 50% of herbicidal effect
3 ... from 51 to 70% of herbicidal effect
4 ... from 71 to 90% of herbicidal effect
5 ... from 91 to 100% of herbicidal effect.
(2) Phytotoxicity:
− ... no damage, ± ... slight damage,
+ ... moderate damage, ++ ... strong damage,
+++ ... extensive damage.

TEST EXAMPLE 2

Effect on the weeds of the crop field (post-emergence treatment)

In the same manner as in Test Example 1, the seeds of the same plants as in Test Example 1 were sown on the soil in a planter, and at the time when each of the plant grew to the first to second leaf-stage, a dilution prepared in the same way as in Test Example 1 from a wettable powder prepared in the same way as in Test Example 1 from a wettable powder prepared in the same way as in Example 2 was uniformly applied on the plants and the surface of the soil in the planter in the same amount as in Test Example 1. The thus treated planter was kept in a glass house at ordinary temperature. On the 21st day of the treatment, the herbicidal activity and the phytotoxicity were observed and evaluated according to the same ratings as in Test Example 1. The results are shown in Table 4.

TEST EXAMPLE 3

Effect on the weeds in the paddy field and phytotoxicity to rice plant in the paddy field After introducing water into a Wagner pot filled with a soil of the ordinary paddy field, thereby covering the soil in the pot with water, the seeds of *Echinochloa Crus-galli* var. *hispidula*, *Scirpus juncoides* subsp. *Hotarui*, *Alisma canaliculatum*, *Monochoria vaginalis* and *Cyperus difformis* were sown on the soil and the tubers of *Sagittaria pygmaea* and *Cyperus serotinus* were planted in the soil. After further transplanting two seedlings of rice plant (variety Sasanishiki) at the two-leaf stage to the pot, the pot was kept in a glass house for 3 days, and then a dilution prepared by diluting an emulsion prepared in the same manner as in Example 3 to a predetermined concentration was uniformly applied onto the surface of water in the pot in the same amount as in Test Example 1 (200 g of the active ingredient per 10 acres). On the 21st day of the treatment, the herbicidal effect on the weeds and the phytotoxicity to the rice plant were observed and evaluated according to the same ratings as in Test Example 1. The results are shown in Table 5.

TABLE 3

| Compound No. | Amaranthus retroflexus | Bidens pilosa var. pilosa | Brassica arvensis | Stellaria media | Solanum nigrum | Abutilon theophrasti | Echinochloa Crus-galli var. frumentacea | Digitaria sanguinalis | Wheat | Corn |
|---|---|---|---|---|---|---|---|---|---|---|
| 1 | 5 | 5 | 5 | 5 | 5 | 5 | 5 | 5 | — | — |
| 2 | 5 | 5 | 5 | 5 | 5 | 5 | 5 | 5 | — | ± |
| 3 | 5 | 5 | 5 | 5 | 5 | 5 | 5 | 5 | — | ± |
| 4 | 5 | 5 | 5 | 5 | 5 | 5 | 5 | 5 | — | — |
| 5 | 5 | 5 | 5 | 5 | 5 | 5 | 5 | 5 | — | — |
| 6 | 5 | 5 | 5 | 5 | 5 | 5 | 5 | 5 | — | ± |
| 7 | 5 | 5 | 5 | 5 | 5 | 5 | 5 | 5 | — | ± |
| 8 | 5 | 5 | 5 | 5 | 5 | 5 | 5 | 5 | — | ± |
| 9 | 5 | 5 | 5 | 5 | 5 | 5 | 5 | 5 | — | — |
| 10 | 5 | 5 | 5 | 5 | 5 | 5 | 5 | 5 | — | — |
| 11 | 5 | 5 | 5 | 5 | 5 | 5 | 5 | 5 | — | — |
| 12 | 5 | 5 | 5 | 5 | 5 | 5 | 4 | 5 | — | — |
| 13 | 5 | 5 | 5 | 5 | 5 | 5 | 5 | 5 | — | — |
| 14 | 5 | 5 | 5 | 5 | 5 | 5 | 5 | 5 | — | — |
| 15 | 5 | 5 | 5 | 5 | 5 | 5 | 5 | 5 | — | ± |
| 16 | 5 | 5 | 5 | 5 | 5 | 5 | 5 | 5 | — | ± |
| 17 | 5 | 5 | 5 | 5 | 5 | 5 | 5 | 5 | ± | ± |
| 18 | 5 | 5 | 5 | 5 | 5 | 5 | 5 | 5 | — | ± |
| 19 | 5 | 5 | 5 | 5 | 5 | 5 | 5 | 5 | — | ± |
| 20 | 5 | 5 | 5 | 5 | 5 | 5 | 5 | 5 | — | ± |
| 21 | 5 | 5 | 5 | 5 | 5 | 5 | 5 | 5 | — | ± |
| 22 | 5 | 5 | 5 | 5 | 5 | 5 | 5 | 5 | — | ± |
| 23 | 5 | 5 | 5 | 5 | 5 | 5 | 5 | 5 | — | ± |
| 24 | 5 | 5 | 5 | 5 | 5 | 5 | 5 | 5 | — | ± |
| 25 | 5 | 5 | 5 | 5 | 5 | 5 | 5 | 5 | — | ± |
| 26 | 5 | 5 | 5 | 5 | 4 | 5 | 3 | 4 | — | — |
| 27 | 5 | 5 | 5 | 5 | 5 | 5 | 4 | 4 | — | ± |
| 28 | 5 | 5 | 5 | 5 | 3 | 5 | 4 | 4 | — | ± |
| 29 | 5 | 5 | 5 | 5 | 5 | 5 | 5 | 5 | — | — |
| 30 | 5 | 5 | 5 | 5 | 5 | 5 | 5 | 5 | — | ± |
| 31 | 5 | 5 | 5 | 5 | 5 | 5 | 5 | 5 | — | ± |
| 32 | 5 | 5 | 5 | 5 | 5 | 5 | 4 | 4 | — | — |
| 33 | 5 | 5 | 5 | 5 | 2 | 5 | 4 | 4 | — | ± |
| 34 | 5 | 5 | 5 | 5 | 5 | 5 | 5 | 5 | — | ± |

TABLE 4

| Compound No. | Amaranthus retroflexus | Bidens pilosa var. pilosa | Brassica arvensis | Stellaria media | Solanum nigrum | Abutilon theophrasti | Echinochloa Crus-galli var. frumentacea | Digitaria sanguinalis | Wheat | Corn |
|---|---|---|---|---|---|---|---|---|---|---|
| 1 | 5 | 5 | 5 | 5 | 5 | 5 | 4 | 4 | — | — |
| 2 | 4 | 5 | 5 | 5 | 5 | 5 | 3 | 4 | — | ± |
| 3 | 2 | 5 | 5 | 5 | 5 | 5 | 3 | 3 | — | ± |
| 4 | 5 | 5 | 5 | 5 | 4 | 5 | 3 | 3 | — | — |
| 5 | 3 | 5 | 5 | 5 | 5 | 5 | 3 | 4 | — | — |
| 6 | 3 | 5 | 5 | 5 | 5 | 5 | 3 | 4 | — | ± |
| 7 | 4 | 5 | 5 | 5 | 5 | 3 | 2 | 2 | — | ± |
| 8 | 5 | 5 | 5 | 5 | 5 | 5 | 4 | 4 | — | ± |
| 9 | 4 | 5 | 5 | 5 | 5 | 4 | 2 | 2 | — | — |
| 10 | 5 | 5 | 5 | 5 | 5 | 5 | 4 | 4 | — | — |
| 11 | 5 | 5 | 5 | 5 | 5 | 5 | 4 | 4 | — | — |
| 12 | 5 | 5 | 5 | 5 | 5 | 4 | 3 | 3 | — | — |
| 13 | 5 | 5 | 5 | 5 | 5 | 5 | 4 | 4 | — | — |
| 14 | 4 | 5 | 5 | 5 | 5 | 4 | 2 | 2 | — | — |
| 15 | 5 | 5 | 5 | 5 | 5 | 5 | 4 | 4 | ± | + |
| 16 | 5 | 5 | 5 | 5 | 5 | 5 | 4 | 5 | ± | + |
| 17 | 5 | 5 | 5 | 5 | 5 | 5 | 4 | 5 | + | ++ |
| 18 | 5 | 5 | 5 | 5 | 5 | 5 | 4 | 4 | ± | ± |
| 19 | 5 | 5 | 5 | 5 | 5 | 5 | 4 | 4 | — | ± |
| 20 | 5 | 5 | 5 | 5 | 5 | 5 | 4 | 5 | ± | + |
| 21 | 5 | 5 | 5 | 5 | 5 | 5 | 4 | 5 | ± | ± |
| 22 | 5 | 5 | 5 | 5 | 5 | 5 | 4 | 4 | ± | ± |
| 23 | 5 | 5 | 5 | 5 | 5 | 5 | 4 | 5 | — | ± |
| 24 | 5 | 5 | 5 | 5 | 5 | 5 | 4 | 5 | + | + |
| 25 | 5 | 5 | 5 | 5 | 5 | 5 | 4 | 5 | + | + |
| 26 | 2 | 5 | 5 | 5 | 3 | 5 | 2 | 2 | — | — |
| 27 | 3 | 5 | 5 | 5 | 4 | 5 | 2 | 2 | — | ± |
| 28 | 5 | 5 | 5 | 5 | 4 | 5 | 3 | 3 | — | ± |
| 29 | 2 | 5 | 5 | 5 | 2 | 5 | 2 | 3 | — | — |
| 30 | 5 | 5 | 5 | 5 | 4 | 5 | 3 | 4 | — | ± |
| 31 | 5 | 5 | 5 | 5 | 4 | 5 | 3 | 3 | — | ± |
| 32 | 2 | 5 | 5 | 5 | 2 | 4 | 2 | 2 | — | — |
| 33 | 5 | 5 | 5 | 5 | 2 | 5 | 3 | 3 | — | ± |
| 34 | 4 | 5 | 5 | 5 | 5 | 5 | 3 | 4 | ± | ± |

TABLE 5

| Compound No. | Echinochloa Crus-galli var. hispidula | Scirpus juncoides subsp. Hotarui | Alisma canaliculatum | Monochoria vaginalis | Cyperus difformis | Sagittaria pygmaea | Cyperus serotinus | rice plant |
|---|---|---|---|---|---|---|---|---|
| 1 | 5 | 5 | 5 | 5 | 5 | 5 | 5 | — |
| 2 | 5 | 5 | 5 | 5 | 5 | 5 | 5 | — |
| 3 | 5 | 5 | 5 | 5 | 5 | 5 | 5 | — |
| 4 | 5 | 5 | 5 | 5 | 5 | 5 | 5 | — |
| 5 | 5 | 5 | 5 | 5 | 5 | 5 | 5 | — |
| 6 | 5 | 5 | 5 | 5 | 5 | 5 | 5 | — |
| 7 | 5 | 5 | 5 | 5 | 5 | 5 | 5 | — |
| 8 | 5 | 5 | 5 | 5 | 5 | 5 | 5 | — |
| 9 | 5 | 5 | 5 | 5 | 5 | 5 | 5 | — |
| 10 | 5 | 5 | 5 | 5 | 5 | 5 | 5 | — |
| 11 | 5 | 5 | 5 | 5 | 5 | 5 | 5 | — |
| 12 | 5 | 5 | 5 | 5 | 5 | 5 | 5 | — |
| 13 | 5 | 5 | 5 | 5 | 5 | 5 | 5 | — |
| 14 | 5 | 5 | 5 | 5 | 5 | 5 | 5 | — |
| 15 | 5 | 5 | 5 | 5 | 5 | 5 | 5 | — |
| 16 | 5 | 5 | 5 | 5 | 5 | 5 | 5 | — |
| 17 | 5 | 5 | 5 | 5 | 5 | 5 | 5 | — |
| 18 | 5 | 5 | 5 | 5 | 5 | 5 | 5 | — |
| 19 | 5 | 5 | 5 | 5 | 5 | 5 | 5 | — |
| 20 | 5 | 5 | 5 | 5 | 5 | 5 | 5 | — |
| 21 | 5 | 5 | 5 | 5 | 5 | 5 | 5 | — |
| 22 | 5 | 5 | 5 | 5 | 5 | 5 | 5 | — |
| 23 | 5 | 5 | 5 | 5 | 5 | 5 | 5 | — |
| 24 | 5 | 5 | 5 | 5 | 5 | 5 | 5 | — |
| 25 | 5 | 5 | 5 | 5 | 5 | 5 | 5 | — |
| 26 | 5 | 4 | 3 | 4 | 5 | 4 | 4 | — |
| 27 | 5 | 5 | 4 | 5 | 5 | 5 | 5 | — |
| 28 | 5 | 3 | 3 | 5 | 5 | 5 | 4 | — |
| 29 | 5 | 5 | 3 | 5 | 5 | 5 | 5 | — |
| 30 | 5 | 5 | 4 | 5 | 5 | 5 | 5 | — |
| 31 | 5 | 5 | 5 | 5 | 5 | 5 | 5 | — |
| 32 | 5 | 3 | 3 | 4 | 3 | 4 | 4 | — |
| 33 | 5 | 5 | 5 | 5 | 5 | 5 | 5 | — |
| 34 | 5 | 5 | 5 | 5 | 5 | 5 | 5 | — |

What is claimed is:

1. A derivative of 1,5-diphenyl-1H-1,2,4-triazole-3-carboxamide represented by the formula (I):

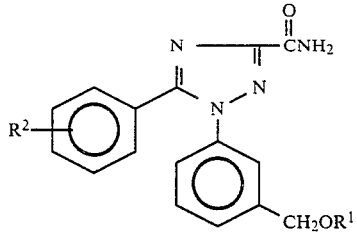

wherein R¹ represents a straight-chain alkyl group of 2 to 10 carbon atoms; a branched-chain alkyl group or cycloalkyl group of 3 to 10 carbon atoms; a (cycloalkyl)alkyl group of 4 to 10 carbon atoms; a non-substituted- or halogen-substituted phenyl group; an aralkyl group of 7 to 9 carbon atoms; an alkenyl group of 3 to 6 carbon atoms or an alkyl group of 2 to 10 carbon atoms, which has been substituted by 1 to 19 fluorine atoms, and R² represents a fluorine atom.

2. A derivative of 1,5-diphenyl-1H-1,2,4-triazole-3-carboxamide according to claim 1, wherein R¹ represents a straight-chain alkyl group of 3 to 6 carbon atoms; a branched-chain alkyl group or cycloalkyl group of 3 to 7 carbon atoms; a ($C_1$-$C_3$)alkyl group; a non-substituted phenyl group; a phenyl group substituted by 1 to 3 chlorine atom(s) and/or fluorine atom(s); an aralkyl group of 7 to 9 carbon atoms; an alkenyl group of 3 to 6 carbon atoms or an alkyl group of 2 to 6 carbon atoms, which is substituted by 3 to 12 fluorine atoms.

3. A derivative of 1,5-diphenyl-1H-1,2,4-triazole-3-carboxamide according to claim 2, wherein said derivative is 1-(3-butoxymethyl)phenyl-5-(2-fluorophenyl)-1H-1,2,4-triazole-3-carboxamide.

4. A derivative of 1,5-diphenyl-1H-1,2,4-triazole-3-carboxamide according to claim 2, wherein said derivative is 5-(2-fluorophenyl)-1-(3-pentyloxymethyl)-phenyl-1H-1,2,4-triazole-3-carboxamide.

5. A derivative of 1,5-diphenyl-1H-1,2,4-triazole-3-carboxamide according to claim 2, wherein said derivative is 5-(2-fluorophenyl)-1-[3-(3-methylbutoxy)methyl]phenyl-1H-1,2,4-triazole-3-carboxamide.

6. A derivative of 1,5-diphenyl-1H-1,2,4-triazole-3-carboxamide according to claim 2, wherein said derivative is 5-(2-fluorophenyl)-1-[3-(2-methylbutoxy)methyl]phenyl-1H-1,2,4-triazole-3-carboxamide.

7. A derivative of 1,5-diphenyl-1H-1,2,4-triazole-3-carboxamide according to claim 2, wherein said derivative is 5-(2-fluorophenyl)-1-[3-(2,2-dimethylpropoxy)methyl]phenyl-1H-1,2,4-triazole-3-carboxamide.

8. A derivative of 1,5-diphenyl-1H-1,2,4-triazole-3-carboxamide according to claim 2, wherein said derivative is 5-(2-fluorophenyl)-1-(3-hexyloxymethyl)-phenyl-1H-1,2,4-triazole-3-carboxamide.

9. A derivative of 1,5-diphenyl-1H-1,2,4-triazole-3-carboxamide according to claim 2, wherein said derivative is 1-[3-(cyclohexylmethoxy)methyl]phenyl-5-(2-fluorophenyl)-1H-1,2,4-triazole-3-carboxamide.

10. A derivative of 1,5-diphenyl-1H-1,2,4-triazole-3-carboxamide according to claim 2, wherein said derivative is 1-[3-(2,2,2-trifluoroethoxy)methyl]phenyl-5-(2-fluorophenyl)-1H-1,2,4-triazole-3-carboxamide.

11. A derivative of 1,5-diphenyl-1H-1,2,4-triazole-3-carboxamide according to claim 2, wherein said derivative is 5-(2-fluorophenyl)-1-[3-(2,2,3,3-tetrafluoropropoxy)methyl]phenyl-1H-1,2,4-triazole-3-carboxamide.

12. A derivative of 1,5-diphenyl-1H-1,2,4-triazole-3-carboxamide according to claim 2, wherein said derivative is 5-(2-fluorophenyl)-1-[3-(2,2,3,3,3-pentafluoropropoxy)methyl]phenyl-1H-1,2,4-triazole-3-carboxamide.

13. A derivative of 1,5-diphenyl-1H-1,2,4-triazole-3-carboxamide according to claim 2, wherein said derivative is 1-[3-(2,2,3,4,4,4-hexafluorobutoxy)methyl]-phenyl-5-(2-fluorophenyl)-1H-1,2,4-triazole-3-carboxamide.

14. A derivative of 1,5-diphenyl-1H-1,2,4-triazole-3-carboxamide according to claim 2, wherein said derivative is 1-[3-(2,2,3,3,4,4,4-heptafluorobutoxy)-methyl]phenyl-5-(2-fluorophenyl)-1H-1,2,4-triazole-3-carboxamide.

15. A derivative of 1,5-diphenyl-1H-1,2,4-triazole-3-carboxamide according to claim 2, wherein said derivative is 1-[3-(2,2,3,3,4,4,5,5-octafluoropentyloxy)-methyl]phenyl-5-(2-fluorophenyl)-1H-1,2,4-triazole-3-carboxamide.

16. A derivative of 1,5-diphenyl-1H-1,2,4-triazole-3-carboxamide according to claim 2, wherein said derivative is 1-[3-(2,2,3,3,4,4,5,5,6,6,7,7-dodecafluoroheptyloxy)methyl]phenyl-5-(2-fluorophenyl)-1H-1,2,4-triazole-3-carboxamide.

17. A herbicidal composition comprising a herbicidally effective amount of a derivative of 1,5-diphenyl-1H-1,2,4-triazole-3-carboxamide represented by the formula (I) as an active ingredient:

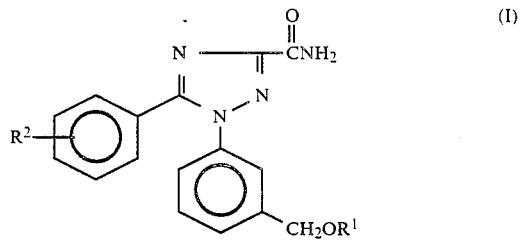

wherein R¹ represents a straight-chain alkyl group of 2 to 10 carbon atoms; a branched-chain alkyl group or cycloalkyl group of 3 to 10 carbon atoms; a (cycloalkyl)-alkyl group of 4 to 10 carbon atoms; a non-substituted- or halogen-substituted phenyl group; an aralkyl group of 7 to 9 carbon atoms; an alkenyl group of 3 to 6 carbon atoms or an alkyl group of 2 to 10 carbon atoms, which has been substituted by 1 to 19 fluorine atoms, and R² represents a fluorine atom, and a herbicidally acceptable carrier or adjuvant.

* * * * *

UNITED STATES PATENT AND TRADEMARK OFFICE
CERTIFICATE OF CORRECTION

PATENT NO. : 4,919,707
DATED : April 24, 1990
INVENTOR(S) : T. Shida et al.

It is certified that error appears in the above-identified patent and that said Letters Patent is hereby corrected as shown below:

Col. 19, line 29, "a $(C_1-C_3)$ alkyl group;" should read

--a $[(C_3-C_7)\text{cycloalkyl}](C_1-C_3)$ alkyl group;--

Signed and Sealed this

Ninth Day of March, 1993

Attest:

STEPHEN G. KUNIN

Attesting Officer

Acting Commissioner of Patents and Trademarks